United States Patent [19]

Yoshida et al.

[11] Patent Number: 5,314,911
[45] Date of Patent: May 24, 1994

[54] IMMUNOSUPPRESSIVE AGENT

[75] Inventors: Tadashi Yoshida, Osaka; Kenzo Koizumi, Sakai; Yoshimi Kawamura, Minoo; Koichi Matsumoto, Toyonaka; Hiroshi Itazaki, Takarazuka, all of Japan

[73] Assignee: Shionogi Seiyaku Kabushiki Kaisha, Osaka, Japan

[21] Appl. No.: 30,884

[22] Filed: Mar. 12, 1993

[30] Foreign Application Priority Data

Mar. 13, 1992 [JP] Japan .................................. 4-089512
Apr. 28, 1992 [JP] Japan .................................. 4-136241

[51] Int. Cl.$^5$ ............................................. A61K 31/35
[52] U.S. Cl. ....................................... 514/451; 549/294
[58] Field of Search ......................... 549/294; 514/451

[56] References Cited

U.S. PATENT DOCUMENTS 4,680,416 7/1987 Hokanson et al. .................. 549/294
4,918,100 4/1990 Hokanson et al. .................. 549/294

FOREIGN PATENT DOCUMENTS 0329361 8/1989 European Pat. Off. .
2219296 12/1989 United Kingdom .

OTHER PUBLICATIONS

Patent Abstracts of Japan, vol. 12, No. 438 (C-544)(3285), Nov. 17, 1988, JP-A-63 165 323, Jul. 8, 1988.
Derwent Publications Ltd., AN 89-036772/05, Jun. 11, 1987, JP-146767, Dec. 19, 1988.
Gan to Kagaku Ryoho, 11(12) Part II, pp. 2674-2680, 1984.
Derwent Publications Ltd., AN 88-231647/33, Jul. 3, 1986, JP-157385, Jul. 8, 1988.
Derwent Publications Ltd., AN 88-238170/34, Jun. 11, 1987, JP-146766, Jul. 14, 1988.

*Primary Examiner*—James H. Reamer
*Attorney, Agent, or Firm*—Oblon, Spivak, McClelland, Maier & Neustadt

[57] ABSTRACT

The present invention relates to a compound represented by the formula I:

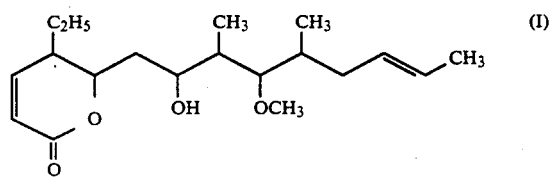

which was isolated from the culture of *Streptomyces prunicolor* PA-48153 and has biological activity such as immunosuppressive activity, antitumor activity and antifungal activity.

5 Claims, No Drawings

IMMUNOSUPPRESSIVE AGENT

BACKGROUND OF THE INVENTION

1. Field of the Invention

This invention relates to a compound represented by the formula I:

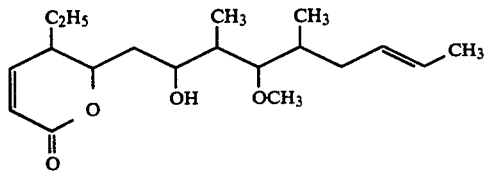

a microorganism producing said compound and a process for preparing said compound.

This invention provides an immunosuppressive agent, an antitumor agent and an antifungal agent which comprise said compound as an effective ingredient.

2. Prior Art

Immunosuppressive agents are indispensable to the prevention of the rejection against the transplantation of organs or tissues and the graft-versus-host reaction by bone marrow transplantation, and to the remedy for autoimmune diseases such as rheumatoid arthritis.

A lot of immunosuppressive agents have been developed and put to clinical use. However, they are not always satisfactory because of their weak and adverse effects. Therefore, new immunosuppressive agents have long been desired.

A lot of antitumor agents have been developed and put to clinical use. As they are somewhat toxic and their doses are therefore limited, the remedy using them is not so satisfactory. An antitumor agent, which is structurally similar to the compound of the present invention, is disclosed in Japanese Patent Kokai 63-165323.

Mycosis is caused by fungi or yeast and is increasing every year. Especially, deepseated mycosis is increasing in connection with AIDS. As agents for deepseated mycosis are exemplified nystatin, amphotericin B, miconazole and 5-fluorocytosine. The development of antifungal agents falls behind that of antibiotics.

An object of this invention is to provide a new compound having immunosuppressive, antitumor and antifungal activities.

SUMMARY

Taking the above-mentioned situation into the consideration, the present inventors found a new compound having immunosuppressive, antitumor and antifungal activities in the culture of Streptomyces prunicolor PA-48153.

This invention relates to a compound represented by the formula I:

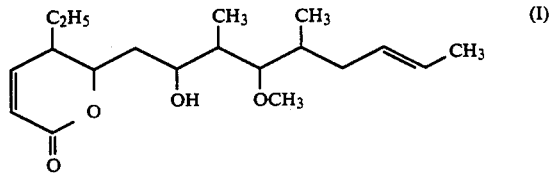

The compound of this invention was confirmed to be (5R*,6R*)-5-ethyl-5,6-dihydro-6-[(E)-(2R*,3S*,4R*,5S*)-2-hydroxy-4-methoxy-3,5-dimethyl-7-nonenyl]-2H-pyran-2-one through X-ray analysis and so on.

A hydroxyl group at position 2 of the side chain nonenyl group of this compound may form an ester with an acid such as carboxylic acid, phosphoric acid or the like and may form an ether.

This invention provides a microorganism belonging to Streptomyces prunicolor and producing the compound of this invention and a process for preparing the compound of this invention, which comprises the following steps;

cultivating a microorganism belonging to the genus Streptomyces and producing said compound in a medium and recovering said compound from the medium.

The compound of this invention has biological activity such as immunosuppressive activity, antitumor activity and antifungal activity and therefore is useful for the prevention of the rejection against the transplantation of organs or tissues and the graft-versus-host reaction by bone marrow transplantation, and for the remedy for autoimmune diseases and cancers such as blood cancers and solid cancers, and is further useful for the prevention and remedy for mycosis.

DESCRIPTION OF THE PREFERRED EMBODIMENTS

Strain PA-48153 belonging to Streptomyces prunicolor of this invention has the following properties.

(1) Morphology: Good growth, abundant aerial mycelium and good spore formation in yeast malt agar, tyrosine agar and Bennett's agar. Simple branching and not spiral. Fairly long spore chain; at least 50 spores per chain. Long cylindrical spore; 0.4–0.5 μm in width and 1.2–1.4 μm in length; and smooth surface under electron microscopic observation. No sporangium, no flagellated spore, and no sclerotium.

(2) Properties on cultivation (28° C., 14 days):

Color names are based on "Color Standard" edited by Japan Color Institute.

TABLE 1

| Agar Medium | Growth | Aerial Mycelium | | Substrate Mycelium | Soluble Pigment |
| | | Formation | Color | | |
| --- | --- | --- | --- | --- | --- |
| Sucrose nitrate agar | Good | Good | White (W) | Pale Yellowish Brown | None |
| Glucose asparagine agar | Good | Good | White/Pale Brown (R) | Pale Yellowish Brown | None |
| Glycerol asparagine agar | Good | Good | Pale Brown (R) | Pale Yellowish Brown | None |
| Inorganic salt starch agar | Good | Good | Pale Brown (R) | Pale Olive Brown | None |
| Tyrosine agar | Good | Good | Pale Orange (R) | Pale Yellowish Brown | None |
| Nutrient agar | Fair | Fair | Pale Brown (R) | Pale Yellowish Brown | None |
| Yeast extract-malt extract agar | Good | Good | Pale Brown (R) | Pale Yellowish Brown | Pale Yellowish Brown (trace) |
| Oatmeat agar | Good | Good | White (W) | Pale Yellowish Brown | None |

TABLE 1-continued

| Agar Medium | Growth | Aerial Mycelium Formation | Aerial Mycelium Color | Substrate Mycelium | Soluble Pigment |
|---|---|---|---|---|---|
| Bennett's agar | Good | Good | Pale Brown (R) | Pale Yellowish Brown | None |

(W): White series of ISP Color Series,
(R): Red series of ISP Color Series

Growth Temperature: 14° to 35° C., optimally 24° to 28° C.
(3) Biological Properties:
Production of Melanoid Pigment: Negative
Tyrosinase Reaction: Negative
Coagulation of Milk: Negative
Peptonization of Milk: Positive
Hydrolization of Starch: Positive.
(4) Utilization of Sugar (Control -):

| L-arabinose | D-xylose | D-glucose |
|---|---|---|
| ++ | ++ | ++ |
| D-fructose | sucrose | inositol |
| ++ | ++ | ++ |
| L-rhamnose | raffinose | D-mannitol |
| ++ | ++ | ++ |

(5) Composition of Cell Wall: LL-2,4-diaminopimelic acid was detected in the whole-cell hydrolysate.

This strain was considered to belong to the genus Streptomyces from the above properties.

As a result of the search of species close to this strain in The Actinomycetes edited by Waksman, vol. 2 (1961), ISP (International Streptomyces Project) Report of Shirling & Gottlieb [International Journal of Systematic Bacteriology, vol. 18, pp. 69-189, pp 279-392 (1968), vol. 19, pp. 391-512 (1969), vol. 22, pp. 265-394 (1972)], Bergey's Manual of Determinative Bacteriology 8th edition (1974), Bergey's Manual of Systematic Bacteriology Vol. 4 (1989) and other documents relating to actinomycetes, this strain was the closest to Streptomyces prunicolor Ryabova and Preobrazhenskaya. This strain was simultaneously compared with Streptomyces prunicolor ATCC 25487. Main properties of the two strains were identical except growth, spore formation and utilization of sucrose. Therefore, this strain was identified as Streptomyces prunicolor and named Streptomyces prunicolor PA-48153.

This strain has been deposited with Fermentation Research Institute, Agency of Industrial Science and Technology at 1-3, Higashi 1 chome, Tsukuba-shi, Ibaraki-ken 305 as Streptomyces prunicolor PA-48153 with accession No. FERM BP-3754 under the Budapest treaty since Feb. 20, 1992.

A general process for preparing the compound of this invention is described below.

A strain belonging to the genus Streptomyces, for example, Streptomyces prunicolor PA-48153 is cultivated in a medium usually used for the conventional fermentation. The medium contains a carbon source, a nitrogen source and inorganic salts in general. As occasion demands, vitamins and precursors may be added to the medium. The carbon source includes glucose, soluble starch, dextrin, glycerol, sugars, organic acids and the like, or the mixture thereof. The nitrogen source includes soybean powder, corn steep liquor, meat extract, yeast extract, cotton seed powder, peptone, wheat malt, ammonium sulfate, ammonium nitrate, and the like, or the mixture thereof. The inorganic salts include calcium carbonate, sodium chloride, potassium chloride, magnesium sulfate, cupric sulfate, manganese chloride, zinc sulfate, cobalt chloride, phosphates and the like.

The cultivation is carried out at 14°-35° C., preferably 20°-28° C. The cultivation time, which depends on the scale of the cultivation, is about 3-5 days for the mass-cultivation. In case of vigorous foaming, antifoam agents such as vegetable oil, lard and polypropyleneglycol may be added to the medium before or during the cultivation.

After the cultivation, the compound of this invention can be recovered from the culture by the conventional methods usually used for recovering fermentation products, that is, filtration, centrifugation, absorption-elution and chromatography with use of various ion exchange resins or other active absorbents, extraction with use of various organic solvents, and the combination thereof.

The physicochemical properties and structure of the compound PA-48153C obtained by the above process are described below.

1) Solubility: soluble in n-hexane, ethyl acetate, chloroform, methanol insoluble in water.
2) Appearance: colorless needles.
3) Melting Point: 78°-79° C.
4) Molecular Formula: $C_{19}H_{32}O_4$ (m.w. 324).
5) SIMS: m/z 325 $(M+H)^+$.
6) Elemental Analysis: Calcd. for $C_{19}H_{32}O_4$: C, 70.33; H, 9.94. Found: C, 70.08%; H, 9.86%.
7) $[\alpha]_D^{23.5}$: $-148.7\pm3.7°$ (C=0.5, $CHCl_3$).
8) UV: $\lambda_{max}^{MeOH}$ nm: end absorption.
9) IR: $\nu_{max}^{KBr}$ cm$^{-1}$: 3505, 1728, 1620, 1460, 1385, 1319, 1286, 1269, 1142, 1095, 1075, 1030, 987, 964, 938, 843, 818.
10a) $^1$H NMR in $CDCl_3$ ppm (J=Hz): 7.01 (1H, dd, J=6.0, J=9.8), 6.03 (1H, dd, J=1.0, J=9.6), 5.54-5.29 (2H, m), 4.78-4.70 (1H, m), 4.25-4.16 (1H, m), 3.48 (3H, s), 3.45 (1H, d, J=2.6), 2.99 (1H, dd, J=4.4, J=6.2), 2.35-2.23 (1H, m), 2.15-2.03 (1H, m), 1.95-1.38 (10H, m), 1.02-0.93 (9H, m).
10b) $^1$H NMR in $C_6D_6$ ppm (J=Hz): 6.14 (1H, dd, J=5.8, J=9.8), 5.80 (1H, dd, J=1, J=9.8), 5.52-5.27 (2H, m), 4.68-4.60 (1H, m), 4.44-4.36 (1H, m), 3.17 (1H, d, J=2.6), 3.11 (3H, s), 2.76 (1H, dd, J=4.4, J=6.4), 2.10-1.98 (1H, m), 1.90-1.74 (2H, m), 1.74-1.55 (7H, m), 1.34-1.07 (2H, m), 0.96 (3H, t, J=4.4), 0.92 (3H, t, J=4), 0.60 (3H, t, J=7.4).
11) $^{13}$C NMR in $CDCl_3$ ppm: 165.22, 151.21, 129.18, 127.38, 121.24, 91.53, 78.11, 67.81, 62.06, 39.53, 39.35, 37.70, 37.15, 36.56, 21.23, 18.45, 15.69, 12.65, 11.47.
12) TLC*: Rf=0.51
13) HPLC**: Retention Time=11.6 min.

*TLC: Merck KGF, Detection; UV (weak), Iodine, and sulfuric acid/heat, Solvent; chloroform/methanol (97:3) Rf=0.51 or n-hexane/ethanol (1:1) Rf=0.25.
**HPLC: Column; COSMOSIL 5C18-AR 4.6φ×150 mm, Detection; UV (220 nm), Solvent; 50% acetonitrile/1% trifluoroacetic acid, Flow rate; 1 ml/min.

This invention provides an antitumor agent, an immunosuppressive agent and an antifungal agent which comprise the compound of this invention as an effective ingredient.

The antitumor agent, the immunosuppressive agent and the antifungal agent of this invention can be administered orally in pharmaceutical forms such as tablets, capsules, granules, powders, syrups and the like; intravenously, intramuscularly and subcutaneously as injections; and percutaneously as ointments.

Tablets can be prepared by compressing the effective ingredient together with supplemental ingredients. These supplemental ingredients include pharmaceutically acceptable vehicles; binders such as corn starch, fillers such as lactose and microcrystalline cellulose, disintegrators such as starch sodium glycolate and lubricants such as magnesium stearate. Tablets may be coated.

Liquid preparations such as syrups, solutions and suspensions can be prepared according to the conventional methods with use of suspending agents such as methylcellulose, emulsifying agents such as lecithin and preservatives.

Injections may be solutions, suspensions and oily or aqueous emulsions containing stabilizers, dispersers or the like.

A dose of the effective ingredient, which depends upon a pharmaceutical form and condition, age, body weight and sex of a patient, is 0.01–50 mg, preferably 0.1–10 mg, per body weight (kg) per day as an antitumor agent, 0.1–50 mg, preferably 2–25 mg, as an immunosuppressive agent and 10–100 mg as an antifungal agent. However, a dose is not limited within the above ranges.

This invention is detailed in the following Example.

EXAMPLE

1. Fermentation

*Streptomyces prunicolor* PA-48153 was inoculated from the seed culture slant into a 2 L-Erlenmeyer flask charged with 800 ml of a medium (adjusted to pH 7 with 2N sodium hydroxide) containing 0.5% soluble starch, 0.5% glucose, 0.5% polypeptone (NIHON PHARMACEUTICAL CO., LTD.), 0.25% meat extract (Difco), 0.5% yeast extract (Difco), 0.25% salt and water, and was subjected to a shake culture with a stroke of 70 mm and 180 r.p.m. at 28° C. for 48 hr. This culture (800 ml) was implanted in a 30 L-jar fermenter charged with 16 L of the medium as described above and incubated with an aeration of 12.8 L/min, an internal pressure of 0.35 kg/cm$^2$ and 200 r.p.m. at 28° C. for 24 hr. This culture (8 L) was implanted in a 250 L-tank charged with 150 L of a medium (adjusted to pH 7.0 with 2N sodium hydroxide) containing 2.0% glucose, 2.0% potato starch, 2.0% defatted soybean powder, 0.5% yeast extract (Difco), 0.25% salt, 0.0005% zinc sulfate heptahydrate, 0.0005% manganese chloride tetrahydrate, 0.0005% cupric sulfate pentahydrate, 0.35% calcium carbonate, 0.003% antifoam agent P-2000 (Dainippon Ink & Chemicals Inc.) and water, and was incubated with an aeration of 120 L/min, an internal pressure of 0.35 kg/cm$^2$ and 280 r.p.m. at 28° C. for 90 hr.

2. Separation and Purification (1) Separation (a) The culture (98 L) obtained above was centrifuged by S-type ultracentrifuge (No. 6-P, Kansai Centrifugal Separator M.F.G. Co., Ltd.) at 15,000 r.p.m. to give 83 L of the supernatant. This supernatant was adjusted to pH 7.0 with 2N hydrochloric acid and extracted with 46 L of ethyl acetate. The extract (40 L) was concentrated under reduced pressure to give 18.91 g of crude product (crude-1).

The microorganisms (wet weight 8 kg) obtained in the above centrifugation as a precipitate was extracted with 28 L of acetone. The solvent was removed by an evaporation to give 6 L of water layer, which was adjusted to pH 7.0 with 2N hydrochloric acid and extracted with 13 L of ethyl acetate. The extract (12 L) was concentrated under reduced pressure to give 22.86 g of crude product (crude-2).

(b) The crude product (crude-1) (18.91 g), the extract of the filtrate, was washed with 300 ml of n-hexane. After the washing, n-hexane was evaporated under reduced pressure to give 5.1 g of a residue (residue-1). Crude product (residue-2) washed by hexane was suspended in 20 ml of ethyl acetate and extracted with 300 ml of hexane. The hexane layer was evaporated under reduced pressure to give 3.1 g of a residue (residue-3). The precipitate (residue-4) obtained by removing the hexane layer was treated in the same manner as crude product (residue-2) to give a residue (residue-5) from the hexane layer and a precipitate (residue-6).

(c) Crude product (crude-2) (22.86 g), the extract of the microorganisms, was washed with 300 ml of n-hexane. After the washing, hexane was evaporated under reduced pressure to give 18.2 g of a residue (residue-11). Crude product (residue-12) washed with hexane was suspended in 20 ml of ethyl acetate and extracted with 300 ml of hexane to give 0.65 g of a residue (residue-13) from the hexane layer and 2.1 g of a precipitate (residue-14).

(2) Purification (a) A fraction containing PA-48153C (residues-1, 3 and 5, 10.4 g in total) separated from the crude product (crude-1) was subjected to column chromatography (column; SiO$_2$, 120 ml (Merck), solvent; chloroform, fraction; 20 g each) to give 4.2 g of partially purified PA-48153C from fractions 9–17. The partially purified PA-48153C was subjected to column chromatography (column; Lobar SiO$_2$ 60 B size (Merck), solvent; n-hexane:ethyl acetate=3:1, fraction; 10 g each) to give 1.6 g of purified PA-48153C from fractions 38–90, which was further subjected to column chromatography (column; Lobar SiO$_2$ 60 B size (Merck), solvent; chloroform:methanol=98:2, fraction; 10 g each) to give 1.39 g of purified PA-48153C from fractions 15–21. The resulting purified PA-48153C was recrystallized from 4 ml of n-hexane to give 965 mg of crystal of PA-48153C (HPLC purity: 98%).

(b) A fraction containing PA-48153C (residues-11 and 13, 18.8 g in total) separated from the crude product (crude-2) was subjected to column chromatography (column; SiO$_2$, 150 ml (Merck), solvent; chloroform, fraction; 20 g each) to give 4.14 g of partially purified PA-48153C from fractions 15–57. The partially purified PA-48153C was subjected to column chromatography (column; Lobar SiO$_2$ 60 B size (Merck), solvent; hexane:ethyl acetate=3:1, fraction; 10 g each) to give 920 mg of purified PA-48153C from fractions 33–57, which was further subjected to column chromatography (column; Lobar SiO$_2$ 60 B size (Merck), solvent; chloroform:methanol=98:2, fraction; 15 g each) to give 750 mg of purified PA-48153C from fractions 9–11. The resulting purified PA-48153C was recrystallized from hexane to give 530 mg of crystal of PA-48153C (HPLC purity: 98%).

Through the above process, 1,495 mg of crystal of PA-48153C in total was obtained.

REFERENTIAL EXAMPLE

In the case of the small scale cultivation, the filtrate of the culture was extracted with ethyl acetate ester to give a residue. PA-48153C was separated from the residue, purified by TLC and recrystallized. In brief, 6 L of the culture was filtered and the resulting filtrate (4.8 L) was extracted with 2 L of ethyl acetate (pH 7.0) to give 437 mg of a residue. The residue was subjected to TLC (KGF (Merck), solvent; 3% methanol/chloroform) to give 57 mg of purified PA-48153C. The purified PA-48153C was recrystallized from n-hexane to give 45 mg of crystal of PA-48153C.

3. Biological Activity

PA-48153C of this invention has biological activity such as immunosuppressive activity, antitumor activity and antifungal activity as described in the following Experiment. Therefore, this compound is useful for the prevention of the rejection against the transplantation of organs or tissues and the graft-versus-host reaction by bone marrow transplantation, and is useful also for the remedy for autoimmune diseases and cancers such as blood cancers and solid cancers, and is further useful for the prevention and remedy for mycosis.

Experimental Example is described below.

1) Effect of PA-48153C on mitogenic responses

Splenic mononuclear cells ($5 \times 10^5$) from C3H/HeN mice were suspended in 0.2 ml of RPMI 1640 medium containing 10% fetal bovine serum and $5 \times 10^{-5}$ M 2-mercaptoethanol (RPMI/FCS) and plated 96-well microtiter plates. The cells were cultured with 5 µg/ml of Concanavalin A (Con A; Type IV, Sigma Chemical Co.) for 72 hr at 37° C. in a humidified atmosphere of 5% carbon dioxide and 95% of air. PA-48153C was dissolved in dimethyl sulfoxide (DMSO) and added to the mitogenic response. The final concentration was not more than 100 ng/ml. Eighteen hours before harvesting, 0.5 µCi of tritiated thymidine ([$^3$H]-TdR) was added to each well. The cells were harvested onto glass filter paper using a semi-automated multiple cell harvester, and [$^3$H]-TdR incorporation was determined by liquid scintillation counter. The results were shown in Table 2.

TABLE 2

| Effect of PA-48153 against Con A reaction of mouse splenic cell | | |
|---|---|---|
| PA-48153C (ng/ml) | Radioactivity cpm ± SD | Inhibition % |
| 0 | 63,100 ± 1,000 | 0 |
| 5.6 | 24,200 ± 883 | 61.6 |
| 1.7 | 10,200 ± 451 | 83.8 |
| 50.0 | 3,780 ± 141 | 94.0 |

IC$_{50}$ (ng/ml): 4.8

As shown in Table 2, PA-48153C inhibited the proliferative response of splenic mononuclear cell from normal mice to Con A in a dose-dependent fashion.

2) Effect of PA-48153C on allogenic Mixed Lymphocyte Reaction (allo-MLR) in vitro Induction and assay of allo-MLR were performed in 96 well microtiter plates. C3H/HeN (H-2$^k$) mouse splenic mononuclear cells ($5 \times 10^5$ cells in 0.1 ml of RPMI/FCS) were mixed with an equal volume of mitomycin C-treated (50 µg/ml, 37° C., 30 min, washed 3 times with RPMI 1640) C57BL/6 (H-2$^b$) mouse splenic mononuclear cells ($5 \times 10^5$ cells) and incubated with RPMI/FCS in 96 well microtiter plate for 6 days under the same condition as described in 1). PA-48153C was added to the allo-MLR in such a manner that its final concentration was not more than 100 ng/ml. Eighteen hours before harvesting, 0.5 µCi of [$^3$H]-TdR was pulsed to each well. The cells were harvested and assayed for allo-MLR by their ability to uptake [$^3$H]-TdR incorporation. As a result, IC$_{50}$ value of PA-48153C inhibiting allo MLR was 3.1 ng/ml.

3) Inhibition of cell growth by PA-48153C

Each cell defined in Table 3 was put in each well of a 96-well microtiter plate in one 0.1 ml-scale containing the defined number of cells and preincubated for one day under the same condition as in 1). PA-48153C (0.1 ml) was added to each well in such a manner that its final concentration was in a range from 0 to 5,000 ng/ml. After 3–4 days incubation, 25 µl of 6 mg/ml MTT [3-(4,5-dimethylthiazol-2-yl)-2,5-diphenyltetrazolium bromide] (Sigma) was added to each well. After further incubation at 37° C. for 4 hr under the same condition, formazan generated therein was dissolved by adding 50 µl of 20% sodium dodecylsulfonate (SDS) in 0.02N HCl and allowing to stand at 37° C. for 24 hr. An amount of formazan generated in proportion to the number of live cells was determined according to optical density analyzed by an immunoreader (Sanko Junyaku k.k.) equipped with a 570 nm-filter (reference to J. Immunol. Methods 65, 55–63 (1983)). IC$_{50}$ (concentration inhibiting 50% cell growth) was calculated from the correlativity of PA-48153C concentration with optical density. The result is shown in Table 3.

TABLE 3

| Inhibition of cell growth by PA-48153C | | | | |
|---|---|---|---|---|
| Cell | Source | Medium[1] | Cell No./Well | IC$_{50}$ (ng/ml) |
| CCD-19Lu | Human normal lung | MEM | $2 \times 10^4$ | >5000 |
| LU-99 | Human giant-cell carcinoma of lung | RPMI 1640 | $2 \times 10^3$ | 2.2 |
| P388 | Mouse leukemia | RPMI 1640 | $5 \times 10^2$ | 1.8 |
| P388/ADM | Mouse leukemia (multi-resistant carcinoma) | RPMI 1640 | $5 \times 10^2$ | 4.8 |

Medium[1]: MEM means Eagle's MEM fortified with 10% fetal calf serum. RPMI 1640 is the same as described in Experimental Example 1). RPMI 1640 for human cell does not contain 2-mercaptoethanol.

As clear from the above data, PA-48153C is characteristic of;

(1) It strongly inhibits the growth of tumor cells, (2) IC$_{50}$ to normal lung cell CCD-19Lu is at least 2,500 times as much as that to giant-cell carcinoma of lung Lu-99, and (3) It strongly inhibits the growth of multi-resistant carcinoma P388/ADM.

4) Antifungal activity of PA-48153C

Antifungal activity of PA-48153C was determined according to the liquid doubling dilution method using Sabouraud or YNB broth. After incubation at 37° C. for 24 or 48 hr, minimum inhibitory concentration (MIC, µg/ml) was determined.

Antifungal activity of PA-48153C against fungi such as *Aspergillus fumigatus* IFO 8866 and *Candida albicans* KE-2 is shown in Table 4.

TABLE 4

| MIC of PA-48153C against *Aspergillus fumigatus* IFO 8866 and *Candida albicans* KE-2 | | | |
|---|---|---|---|
| Fungi | Broth | Time | MIC (µg/ml) |
| *Aspergillus fumigatus* IFO 8866 | Sabouraud | 24 | 12.5 |
| *Candida albicans* KE-2 | YNB | 48 | 50 |

We claim:

1. A compound which is (5R*,6R*)-5-ethyl-5,6-dihydro-6-[(E)-(2R*,3S*,4R*,5S*)-2-hydroxy-4-methoxy-3,5-dimethyl-7-nonenyl]-2H-pyran-2-one.

2. A pharmaceutical composition comprising an effective amount of a compound of claim 1 in association with a pharmaceutically acceptable, substantially non-toxic carrier or excipient.

3. An immunosuppressive agent which comprises the compound of claim 1 as an effective ingredient.

4. An antitumor agent which comprises the compound of claim 1 as an effective ingredient.

5. An antifungal agent which comprises the compound of claim 1 as an effective ingredient.

* * * * *